United States Patent [19]

Belliotti et al.

[11] Patent Number: 5,212,189

[45] Date of Patent: May 18, 1993

[54] THIADIAZOLE OR OXADIAZOLE ANALOGS OF FENAMIC ACIDS CONTAINING SUBSTITUTED HYDROXAMATE SIDE CHAINS AS ANTIINFLAMMATORY AGENTS

[75] Inventors: Thomas R. Belliotti, Ypsilanti; David T. Connor, Ann Arbor; Catherine R. Kostlan, Saline, all of Mich.

[73] Assignee: Warner-Lambert Company, Morris Plains, N.J.

[21] Appl. No.: 809,686

[22] Filed: Dec. 17, 1991

[51] Int. Cl.$^5$ .............. C07D 271/113; C07D 285/125; A61K 31/41

[52] U.S. Cl. .................... 514/363; 514/364; 548/143; 548/144; 548/136; 548/138

[58] Field of Search .............. 548/138, 143, 136, 144; 514/363, 364

[56] References Cited

U.S. PATENT DOCUMENTS

| | | | |
|---|---|---|---|
| 3,413,313 | 11/1968 | Scherrer | 514/482 |
| 4,092,430 | 5/1978 | Sallmann et al. | 514/482 |
| 4,981,865 | 1/1991 | Belliotti | 514/480 |
| 5,017,604 | 5/1991 | Beliotti et al. | 514/482 |

FOREIGN PATENT DOCUMENTS

| | | |
|---|---|---|
| 039051 | 11/1981 | European Pat. Off. . |
| 401857 | 12/1990 | European Pat. Off. ............ 548/144 |
| 8903818 | 5/1989 | PCT Int'l Appl. . |
| 9001929 | 3/1990 | PCT Int'l Appl. . |
| 212153 | 7/1989 | United Kingdom . |

OTHER PUBLICATIONS

Derwent Abstract 87-130305/19 for NL 8602-610-A & DE 3636413.

*Primary Examiner*—Robert Gerstl
*Attorney, Agent, or Firm*—Ronald A. Daignault

[57] ABSTRACT

The present invention is a novel compound which is a thiadiazole or oxadiazole analog of a fenamic acid having a substituted hydroxamate side chain and pharmaceutically acceptable acid addition or base salts thereof, pharmaceutical compositions and methods of use thereof. The invention compounds are now found to have activity as inhibitors of one or both of cyclooxygenase and 5-lipoxygenase providing treatment of conditions advantageously affected by such inhibition including inflammation, arthritis, pain, fever, and the like. Thus, the present invention is also a pharmaceutical composition or method of use thereof.

23 Claims, No Drawings

THIADIAZOLE OR OXADIAZOLE ANALOGS OF FENAMIC ACIDS CONTAINING SUBSTITUTED HYDROXAMATE SIDE CHAINS AS ANTIINFLAMMATORY AGENTS

BACKGROUND OF THE INVENTION

The present invention is a novel compound which is a thiadiazole or oxadiazole analog of a fenamic acid having a substituted hydroxamate side chain and pharmaceutically acceptable acid addition or base salts thereof, pharmaceutical compositions and methods of use thereof The invention compounds are now found to have activity as inhibitors of one or both of cyclooxygenase and 5 lipoxygenase providing treatment of conditions advantageously affected by such inhibition including inflammation, arthritis, pain, fever, and the like. Thus, the present invention is also a pharmaceutical composition or method of use thereof.

Fenamic acids and hydroxamic acid derivatives of fenamic acids are known antiinflammatory agents, 5-lipoxygenase inhibitors, or cyclooxygenase inhibitors. A few of these references disclosing hydroxamate derivatives of fenamic acids are as follows:

U.S. Pat. No. 4,092,430 disclosing acetohydroxamic acid derivatives of fenamates;

WO 8903818A disclosing N hydroxy(or alkoxy)-N-substituted derivatives and various quinazolinone, indole oxime derivatives or hydroxy imino derivatives of fenamates;

U.S. Pat. No. 5,017,604 disclosing methyl hydroxamate derivatives of fenamic acid;

U.S. Pat. No. 3,413,313 disclosing ketoxime derivatives of fenamic acids;

EP Application No. 81103066.7 disclosing N-aminomethyl-N-acyl hydroxylamine prodrugs of hydroxamic acid derivatives including fenamates;

British 2212153A disclosing C(O)N(OR2)R1 derivatives of pyridyl-substituted phenyl containing groups including fenamate moieties.

These references differ from the present invention by at least the lack of a teaching to the present thiadiazole or oxadiazole derivative group.

Heteroaryl amino or aminoalkyl substituted phenyl hydroxamic acid derivatives are also known as 5-lipoxygenase inhibitors or antiinflammatory agents 15 as shown by the following references, for example:

WO 9001929A discloses among its substituents a furyl, thienyl, thienyl-1,1-dioxide, pyrrolyl, pyridyl, benzofuranyl, benzothienyl, benzothienyl-1,1 dioxide, indolyl, attached through an alkylamino to phenyl hydroxamic acid derivatives; (This appears to be an application related to EP 196184)

NL 8602610A discloses 5 benzoyl N hydroxy-2-thiophene acetamides with suggested substituents on the benzoyl including thienyl, furyl, tetrahydrofuryl, or pyridyl;

EP Application No. 196674 discloses various rings in a hydroxamate derivative including heterocycles.

These references teach compounds which each differ from the present invention by at least the lack of a fenamate ring system.

Heterocycle substituted fenamate derivatives are also known having one or both of the activity of the present invention, i.e., 5-lipoxygenase and cyclooxygenase inhibition. References showing this class of compounds include the following:

U.S. application Ser. No. 07/769,562 shows a thia- or oxadiazole analog of a fenamic acid.

U.S. Pat. No. 4,962,119 shows a triazolyl analog of fenamic acid.

U.S. application Ser. No. 697,822 shows thiazolidinone, oxazolidinone, and imidazolidinone derivatives of fenamates These references teach compounds which each differ from the present invention by at least the lack of a substituted hydroxamate side chain

SUMMARY OF THE INVENTION

The present invention is a compound of the Formula (I)

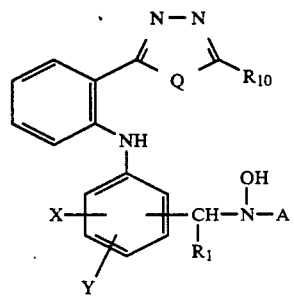

or a pharmaceutically acceptable salt thereof; wherein
Q is S or O;
$R_{10}$ is —OH, —SH, or —NH$_2$;
$R_1$ is H or lower alkyl;
X is H, halogen, lower alkyl, lower alkoxy, CF$_3$, or OH;
Y is H, halogen, lower alkyl, lower alkoxy, CF$_3$, or OH;

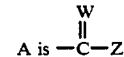

wherein
W is S or O,
Z is lower alkyl, lower alkoxy, NR$_2$R$_3$
wherein R$_2$ and R$_3$ are independently H or lower alkyl.

The present invention is also a pharmaceutical composition for the treatment of conditions advantageously affected by the inhibition of one or both 5 lipoxygenase and cyclooxygenase which comprises an amount effective for the treatment of the condition of a compound of Formula I as defined above or the pharmaceutically acceptable salt thereof together with a pharmaceutically acceptable carrier.

Compounds of this invention are inhibitors of the synthesis of the products of one or both of the enzymes 5-lipoxygenase and cyclooxygenase, and are for the treatment of the conditions meant to include rheumatoid arthritis, osteoarthritis, other inflammatory conditions, psoriasis, pain, allergic diseases, asthma, inflammatory bowel disease, GI ulcers, cardiovascular conditions including ischemic heart disease and atherosclerosis, and ischemia-induced cell damage, particularly brain damage caused by stroke. These conditions can also include acne, sunburn, psoriasis, and eczema. Such conditions are exemplary in nature and are in no way meant to limit the scope of the invention.

Thus, the present invention is also a method for treatment of the condition as noted above in a mammal, including humans, suffering therefrom with a pharmaceutical composition having the compound of Formula I as defined above in unit dosage form. The invention also provides for use of any such compound of Formula I or salt thereof in the manufacture of a medical therapeutic agent.

A pharmaceutical composition of Formula I or use of the compound of Formula I is meant to include treatment understood to be prophylactic pertinent to the foregoing named conditions.

The most preferred compound of the present invention is a compound of the Formula I wherein the compound is N-[1-[2-chloro-3-[[2-(4,5-dihydro-5thioxo-1,3,4-oxadiazol-2-yl) phenyl]amino]phenyl]ethyl]-N-hydroxyacetamide;

N-[1-[3-[[2-(4,5-dihydro-5 thioxo 1,3,4-oxadiazol-2 yl) phenyl]amino]-2 methylphenyl]ethyl]-N-hydroxyacetamide;

N-[1-[3-[[2-(4,5-dihydro-5-thioxo 1,3,4-oxadiazol-2 yl) phenyl]amino]-2,6 dimethylphenyl]ethyl]-N-hydroxyacetamide;

N-[1-[3-[[2-(4,5-dihydro-5-thioxo-1,3,4-oxadiazol-2-yl) phenyl]amino]phenyl]ethyl]-N-hydroxyacetamide;

Ethyl ester of [1-[2-chloro-3-[[2-(4,5-dihydro-5-thioxo-1,3,4 oxadiazol-2-yl) phenyl]amino]phenyl]-ethyl]hydroxycarbamic acid;

N-[1-[2-chloro-3-[[(4,5-dihydro-5-thioxo-1,3,4-oxadiazol-2-yl) phenyl]amino]phenyl]ethyl]-N-hydroxy-N'-methylurea;

N-[1-[2-chloro-3-[[2-(4,5-dihydro-5-oxo-1,3,4-oxadiazol-2-yl) phenyl]amino]phenyl]ethyl]-N-hydroxyacetamide;

N-[1-[3-[[2-(4,5-dihydro-5-oxo-1,3,4-oxadiazol-2-yl) phenyl]amino]phenyl]ethyl]-N-hydroxyacetamide;

Ethyl ester of [1-[2-chloro-3-[[2-(4,5-dihydro-5-oxo-1,3,4-voxadiazol-2-yl) phenyl]amino]phenyl]-ethyl]-hydroxycarbamic acid;

N-[1-[2-chloro-3-[[2-(4,5 dihydro-5-oxo-1,3,4-oxadiazol-2-yl) phenyl]amino]phenyl9 ethyl]-N-hydroxy-N'-methylurea; or N-[1-[2-chloro-3-[[2-(5-amino 1,3,4 oxadiazol-2-yl) phenyl]amino]phenyl]ethyl]-N-hydroxyacetamide.

DETAILED DESCRIPTION OF THE INVENTION

In compounds of Formula I, the term "lower alkyl" includes an alkyl group of from one to six carbons such as methyl, ethyl, propyl, butyl, and the like and branched isomers thereof. The term "lower alkoxy" includes from one to six carbons such as methoxy, ethoxy, propoxy, butoxy, and the like and branched isomers thereof. "Halogen" is chloro, fluoro, iodo, or bromo.

The present invention is meant to include tautomeric forms of the compounds of Formula I. These can be shown as follows:

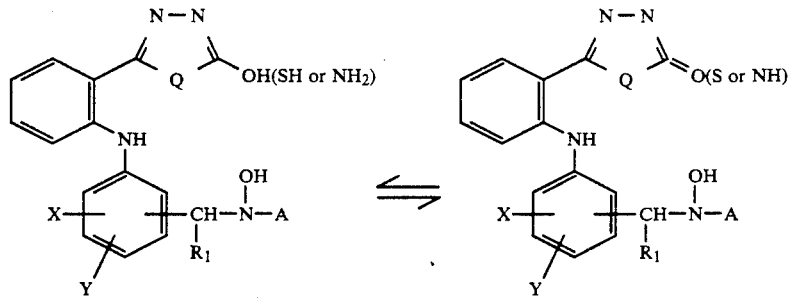

appropriate compounds of Formula I are useful in free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid and benzenesulfonic acid, p-toluenesulfonic acid, and the like, giving the hydrochloride, sulfate, ethanesulfonate, benzenesulfonate, p toluenesulfonate, and the like, respectively; or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono , di-, or trihydroxyalkylamines such as mono-, di-, or triethanolamine; amino acids such as arginine and lysine; chlorine; guanidine; N-methyl glucosamine; n methyl glucamine; 1-glutamine; N-methylpiperazine; morpholine; ethylene diamine; N-benzylphenethylamine; tris(hydroxymethyl) aminoethane; and the like (see for example, "Pharmaceutical Salts", J. Pharm. Sci. 66(1):1–19 (1977)). Salts of inorganic bases include sodium, potassium, calcium, or the like.

The acid addition salts of said basic compounds are prepared either by dissolving the free base or acid of compound I in an aqueous or aqueous alcohol solution or other suitable solvent containing the appropriate acid or base, and isolating the salt by evaporating the solution or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention is meant to include each individual isomer and a mixture thereof. The individual isomers may be prepared or isolated by methods known in the art.

The compounds of this invention may also exist in hydrated or solvated forms.

Thus, pharmaceutical compositions are prepared from compounds of Formula I and salts thereof described as the present invention in unit dosage form comprising the compound either alone or in admixture with a pharmaceutically acceptable carrier appropriately selected from those known.

In determining when a lipoxygenase, cyclooxygenase, or dual lipoxygenase/cyclooxygenase inhibitor is indicated, of course, inter alia, the particular condition in question and its severity, as well as the age, sex, weight, and the like of the subject to be treated must be taken into consideration and this determination is within the skill of the attending physician or veterinarian.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, cachets, lozenges, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an unaffected area (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound of Formula I or pharmaceutically acceptable salt thereof is employed in treatment. The dosage regimen is selected according to a variety of factors including condition of the subject to be treated, severity of symptoms, and the route of administration. In so proceeding, the physician or veterinarian could employ relatively low dosages at first, subsequently increasing the dose until a maximum response is obtained. For convenience, the total daily dosage may be divided and administered in portions during the day if desired.

Initial dosages of the compounds of the invention having Formula I or pharmaceutically acceptable salt thereof are ordinarily in the range of 20 mg up to 25 g per day, orally, preferably 50 mg to 350 mg per dose orally, given from one to four times daily or as needed. When other forms of administration are employed, equivalent doses are administered.

A suitable dose of a compound of Formula I or pharmaceutically acceptable salt thereof for a subject suffering from any condition as described hereinbefore is 0.1 μg to 500 mg of the compound per kilogram body weight. In the case of systemic administration, the dose may be in the range of 0.5 to 500 mg of the compound per kilogram body weight, the most preferred dosage being 0.5 to 500 mg per kilogram body weight administered two to three times daily. In the case of topical administration, e.g., to the skin or eye, a suitable dose may be in the range of 0.1 ng to 100 μg of the compound per kilogram body weight, typically about 0.1 μg/kg.

In the case of oral dosing for the treatment of prophylaxis of arthritis or inflammation in general, due to any cause, a suitable dose of a compound of Formula I or a pharmaceutically acceptable salt thereof, may be as specified in the preceding paragraph, but most preferably is from 1 to 5 mg of the compound per kilogram of body weight, for example, from 1 to 2 mg per kilogram body weight.

While it is possible for an active ingredient to be administered alone, it is preferable to present it as a pharmaceutical formulation comprising a compound of Formula I or a pharmaceutically acceptable acid addition or base salt thereof and a pharmaceutically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, MD).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air 5% carbon dioxide. Cells are harvested by centrifugation. They are washed with cold phosphate-buffered saline, pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL Cells are incubated and without test agent (in DMSO) (1% DMSO is without effect on arachidonic acid metabolism) for 10 minutes at room temperature. Calcium ionophore A23187 (5 μM) is added and cells are incubated for 7 minutes at 37° C. The reaction is stopped by chilling the tubes on ice for 10 minutes. Cells are separated by centrifugation and the supernatant is stored at −20° C. Aliquots (100 μL) are analyzed for $LTB_4$ and $PGF_{2\alpha}$ using radioimmunoassay kits as provided by the supplier.

Table 1 contains biochemical data for compounds of Formula I obtained from this whole cell assay as amount of inhibition at 10 μM or $IC_{50}$s which are calculated as the concentration of a test compound in micromoles (μM) causing 50% inhibition of $LTB_4$ or $PGF_{2\alpha}$ formation.

TABLE 1

| Compound of Example Number | ARBL[a] IC$_{50}$ (μM) | ARBC[b] IC$_{50}$ (μM) |
| --- | --- | --- |
| 13 | 0.68[c] | 1.88[c] |
| 14 | 100% @ 10 | N @ 10[d] |
| 15 | 1.09[c] | 0.86[c] |
| 16 | 1.87[c] | 0.36[c] |
| 7  | 9.59[c] | 1.07[c] |
| 8  | 66% @ 10 | N @ 10[d] |
| 9  | 5.93[c] | >10[d] |
| 10 | N @ 10 | N @ 10 |
| 11 | 1.14[c] | 0.91[c] |
| 12 | N @ 10 | 100% @ 10 |
| 17 | 100% @ 10 | N @ 10 |

[a]Inhibition of LTB$_4$
[b]Inhibition of PGF$_{2α}$
[c]IC$_{50}$
[d]N = Less than 40% inhibition at 10 μM In addition to the compounds of Formula I or a pharmaceutically acceptable salt thereof, the pharmaceutical compositions can also contain other active ingredients, such as cyclooxygenase inhibitors, nonsteroidal antiinflammatory drugs (NSAIDs), peripheral analgesic agents such as zomepirac, diflunisol, and the like. The weight ratio of the compound of the Formula I to the second active ingredient may be varied and will depend upon the effective dose of each ingredient. Generally, an effective dose of each will be used. Thus, for example, when a compound of the Formula I or II or salt thereof is combined with an NSAID, the weight ratio of the Formula I or salt thereof to the NSAID will generally range from about 100:1 to about 1:1000, preferably about 200:1 to 1:200. Combinations of a compound of the Formula I or II and other active ingredients will generally also be within the aforementioned range, but in each case, an effective dose of each active ingredient should be used.

Combinations of a compound of the Formula I or II or salt thereof and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flubiprofen, fenoprofen, fenbufen, pirprofen, earprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, ioxepac, furofenac, tropinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g., —CH$_2$COO$^-$Na$^+$) typically attached directly to a ring system, preferably to an aromatic or heteroaromatic ring system.

Thus, "fenamic acid derivatives" as defined herein are nonnarcotic analgesics/nonsteroidal antiinflammatory drugs which contain the basic structure:

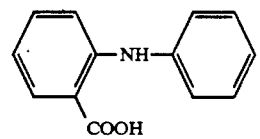

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

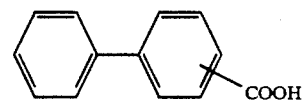

which can bear a variety of substituents and in which the free —COOH group can be in the form of a pharmaceutically acceptable salt group, e.g., —COO$^{-Na+}$.

The oxicams which can be used in the present invention comprise: piroxicam, sudoxicam, isoxicam, and 4-hydroxy-1,2-benzothiazine 1,1-dioxide 4-(N-phenyl) carboxamide. Structurally related oxicams having similar analgesic and antiinflammatory properties are also intended to be encompassed by this group.

Thus, "oxicams" as defined herein are nonnarcotic analgesic/nonsteroidal antiinflammatory drugs which have the general formula:

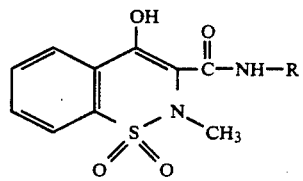

wherein R is an aryl or heteroaryl ring system.

The following NSAIDs may also be used: acemetacin, aminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fenetizole mesylate, fenclofenac, fenclorac, fendosal, fenflumizole, fentiazac, feprazone, floctafenine, flunixin, flunoxaprofen, fluproquazone, fopirtoline, fosfosal, furcloprofein, furofenac, flucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate, sodium, meseclazone, microprofen, nabumetone, nictinodole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudixocam, suprofen, talmetacin, talniflumate, tenoxicam, thiazolinobutazine, thielavin B, tiaprofenic acid, tiaramide HCl, tiflamazole, timegadine, tioxaprofen, tolfenamic acid, tolpadol, tryptamid, ufenamate, and zidometacin.

Finally, NSAIDs which may also b=used include the salicylates, specifically aspirin, and the phenylbutazones, and pharmaceutically acceptable salts thereof.

Pharmaceutical compositions comprising the Formula I compound or salt thereof may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compound of Formula I or salt thereof may also be advantageously combined with an $H_1$ or $H_2$-receptor antagonist, such as for instance, cimetidine, ranitidine, terfenadine, famotidine, temelastine, acrivastine, loratidine, utrizine, tazifylline, azelastine, aminothiadiazoles disclosed in European Patent 81102976.8 and like compounds such as those disclosed in U.S. Pat. No. 4,283,408; 4,362,736; 4,394,508; and European Patent Application 40,696. The pharmaceutical compositions may also contain a $K^+/H^+$-ATPase inhibitor such as omeprazole, disclosed in U.S. Pat. No. 4,255,431, and the like. Each of the references referred to in this paragraph is hereby incorporated by reference.

Generally, the scheme for the preparation of the compounds of Formula I above is shown in Scheme I and Scheme II as follows:

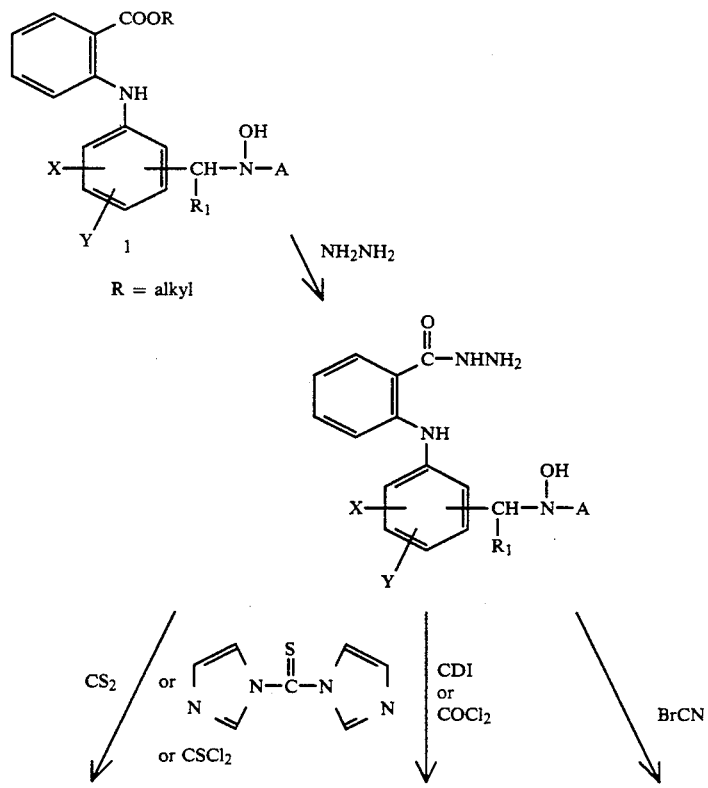

Scheme I

-continued
Scheme I
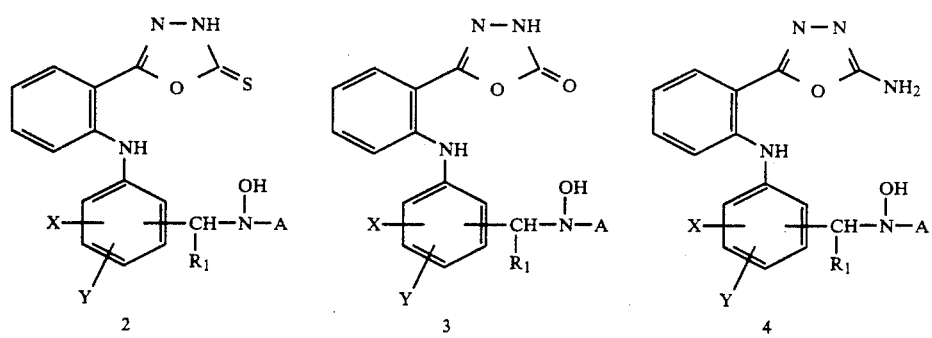
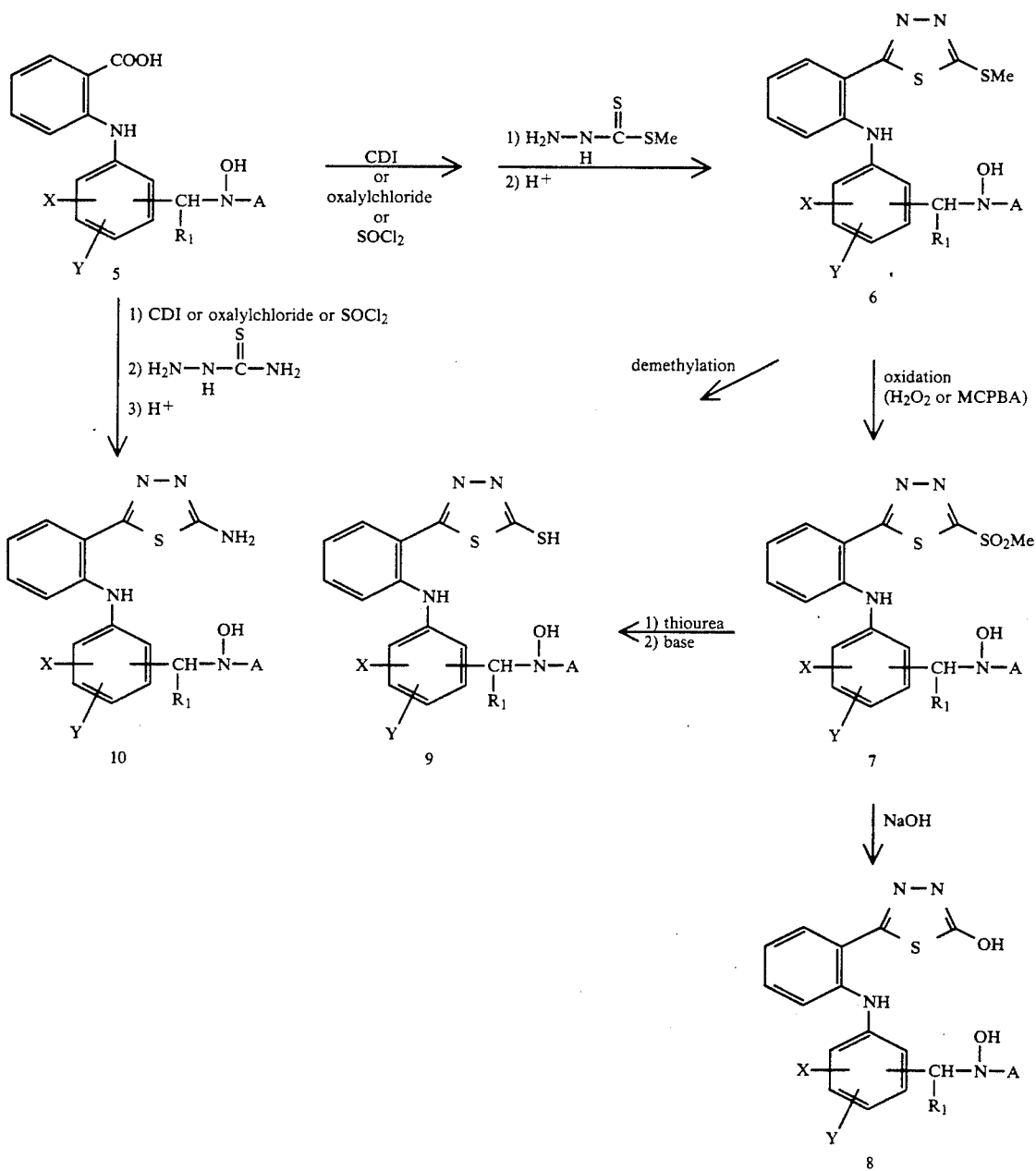

Scheme I

The starting esters (1) are prepared as described in U.S. Pat. No. 5,017,604. Intermediate hydrazides may be prepared from the corresponding esters (1) by treatment with hydrazine at 0° C. to room temperature, preferably anhydrous hydrazine in the absence of another solvent at room temperature for 5 to 30 minutes Thiones 2 may be prepared from the hydrazides by treatment with a reagent such as carbon disulfide or thiophosgene or thiocarbonyldiimidazole in an alcohol solvent such as methanol or an ether solvent such as THF in the presence of an appropriate base such as NaOH, KOH, triethylamine, imidazole, and the like. The reactions may be conducted at temperatures of 0° C. to the reflux temperature of the solvent for 30 minutes to overnight. Oxo derivatives 3 may be prepared from the hydrazides by treatment with a reagent such as phosgene or carbonyldiimidazole in an alcohol solvent such as methanol or an ether solvent such as THF in the presence of an appropriate base such as NaOH, KOH, triethylanine, imidazole, and the like. The reactions may be conducted at temperatures of 0° C. to the reflux temperatures of the solvent for 30 minutes to overnight. Amino derivatives 4 may be prepared from the corresponding hydrazide by treatment with a reagent such as cyanogen bromide in an ether solvent such as dioxane or THF in the presence of an appropriate base such as sodium bicarbonate at a temperature of 0° C. to the reflux temperature of the solvent.

Scheme II

Thiadiazoles 6 may be prepared from carboxylic acids 5 (prepared as described in U.S. 5,017,604) by activation of the carboxylic acid with a reagent such as carbonyldiimidazole followed by treatment with methyl hydrazinecarbodithioate and then cyclization. Alternatively, the carboxylic acid may be activated by treatment with a reagent such as oxalyl chloride or thionyl chloride or the like. Amino compounds 10 may be prepared from carboxylic acids 5 by activation of the carboxylic acid with a reagent such as carbonyldiimidazole followed by treatment with thiosemicarbazide and then cyclization under acidic conditions. Alternatively, the carboxylic acid may be activated by treatment with a reagent such as oxalyl chloride or thionyl chloride or the like. Compound 9 may be prepared by demethylation of 6 or alternatively by oxidation of 6 to the sulfone 7 using a reagent such as MCPBA or hydrogen peroxide followed by reaction with thiourea and then sodium hydroxide. Compound 8 may be prepared by hydrolysis of sulfone 7 using reagents such as sodium hydroxide in an alcohol solvent.

Conditions within the description of Schemes I and II above and variations in the description are known or can be readily determined from analogous reactions known to one of ordinary skill in the art.

Those compounds that contain an acidic proton can be converted to salts via treatment with an organic or inorganic base.

Generally, starting materials are known, commercially available, or can be prepared by known methods.

Under certain circumstances as discussed above, it is necessary to protect either the N or O of intermediates. Introduction and removal of such suitable oxygen and nitrogen protecting groups are well known in the art of organic chemistry; see for example, "Protective Groups in Organic Chemistry," J. F. W. McOmie, *Advances in Organic Chemistry* 3:159-190 (1963); J. F. W. McOmie, *Chem. & Ind.* 603 (1979), and T. W. Greene, "Protective Groups in Organic Synthesis," Wiley (New York) 1981, Chapters 2, 3, and 7.

Examples of suitable oxygen protecting groups are benzyl, t-butyl-protecting groups, ethoxyethyl, methoxyethoxymethyl, and the like. Protection of an N H containing moiety is necessary for some of the processes described herein for the preparation of compounds of this invention. Suitable nitrogen protecting groups are benzyl, triphenylmethyl, trialkylsilyl, trichloroethyl carbamate, trichloroethoxycarbonyl, vinyloxycarbamate acetyl, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis and t butyldimethylsilyl being removed by reaction with, for example, tetra n-butylammonium fluoride.

In the process described herein for the preparation of compounds of this invention, the requirements for protective groups are generally well recognized by one skilled in the art of organic chemistry, and accordingly the use of appropriate protecting groups is necessarily implied by the processes of the schemes herein, although not expressly illustrated.

The products of the reactions described herein are isolated by conventional means such as extraction, distillation, chromatography, crystallization, and the like The invention is further elaborated by the representative examples as follows. Such examples are not meant to be limiting.

EXAMPLE 1

2-[[3-[1-(Acetylhydroxyamino)ethyl]-2-chlorophenyl]-amino]benzoic acid hydrazide 2[[3-[1-(Acetylhydroxyamino)ethyl]-2-chlorophenyl]amino]benzoic acid methyl ester (4.0 g, 11.0 mmoles) is suspended in neat hydrazine (30 mL) and stirred at room temperature. When all solid is dissolved (approximately 10 minutes after addition) the reaction mixture is diluted with 300 mL of cold brine. The pH of the solution is lowered to pH 7 by the addition of concentrated HCl. The precipitate is collected by filtration and recrystallized from EtOAc to give 2-[[3-[1-(acetylhydroxyamino]ethyl]-2-chlorophenyl]amino]benzoic acid hydrazide (2.8 g, 69%); m.p. 193°-195° C.

The following compounds are prepared by a procedure analogous to that of Example 1 using appropriately corresponding starting materials.

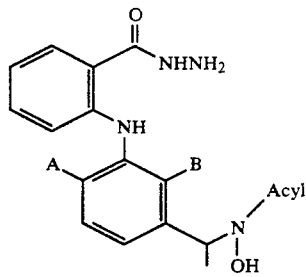

| Example | A | B | Acyl | % Yield | M.P. |
|---|---|---|---|---|---|
| 2 | H | H | Ac | 87 | Oil |
| 3 | H | Cl | CO$_2$Et | 84 | 132–134° C. |
| 4 | H | Cl | CONHMe | 83 | 178–179° C. |
| 5 | H | Me | Ac | 50 | 194–196° C. dec. |
| 6 | Me | Me | Ac | 74 | 183–184° C. |

EXAMPLE 7

N-[1-[3-[[2-(4,5-Dihydro-5-thioxo-1,3,4 oxadiazol-2-yl) phenyl]amino]-2-chlorophenyl]ethyl]-N-hydroxy Acetamide A solution of 2-[[3-[1-(acetylhydroxyamino)ethyl]-2-chlorophenyl]amino]benzoic acid hydrazide (1.0 g, 2.8 mmoles) and KOH (0.17 g, 3.0 mmoles) in 50 mL MeOH is stirred at room temperature until all solids are dissolved. Carbon disulfide (0.48 g, 6.3 mmoles) is added and the reaction mixture is heated at reflux for 18 hours. After being cooled to room temperature, the reaction mixture is acidified to pH 5 with concentrated HCl and the methanol is removed on the rotovap. The organics are extracted into EtOAc (3 × 50 mL). The combined organic extracts are washed with water (2 × 50 mL) and 50 mL of brine. Drying over MgSO$_4$ and evaporation of solvent gives an off-white solid. Recrystallization from H$_2$O/MeOH gives 0.31 g (27%) of N-[1-[3-[[2-(4,5-dihydro-5-thioxo-1,3,4-oxadiazol-2-yl) phenyl]amino]-2-chlorophenyl]ethyl-N-hydroxyacetamide, m.p. 205°–207° C.

The following compounds are prepared according to a procedure analogous to that of Example 7 using appropriate corresponding materials.

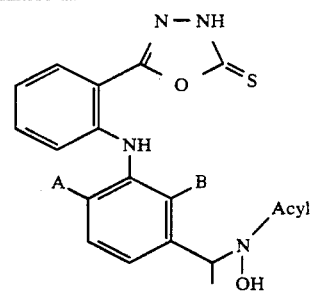

| Prepared from Compound of Example | Example | A | B | Acyl | % Yield | M.P. °C. |
|---|---|---|---|---|---|---|
| 5 | 8 | H | Me | Ac | 66 | 201–202 dec. |
| 6 | 9 | Me | Me | Ac | 30 | 202–204 dec. |
| 2 | 10 | H | H | Ac | 35 | 200–201 |
| 3 | 11 | H | Cl | CO$_2$Et | 30 | 212–213 |
| 4 | 12 | H | Cl | CONHMe | 39 | 213–214 |

EXAMPLE 13

N-[1-[3-[[2-(4,5-Dihydro-5oxo-1,3,4-oxadiazol-2-yl) phenyl]amino[-2-chlorophenyl]ethyl]-N-hydroxyacetamide CDI (0.63 g, 3.9 mmoles) is added to a solution of 2-[[3-[1-(acetylhydroxyamino)ethyl]-2-chlorophenyl]amino]benzoic acid hydrazide (1.4 g, 3.9 mmoles) and triethylamine (0.81 g, 8.1 mmoles,) in 25 mL of THF at 0° C. under an argon atmosphere. The reaction mixture is stirred at 0° C. for 30 minutes under Ar, and then at room temperature overnight. The reaction mixture is partitioned between 50 mL of 1.0 N HCl and 50 mL of EtOAc. The organic layer is washed with 100 mL of 1.0 N HCl, 100 mL of water, and 100 mL of brine. Drying over MgSO$_4$ and evaporation of the solvent gives an off white solid. Flash chromatography over silica gel in EtOAc gives 0.27 g (18%) of N-[1-[3-[[2-(4,5-dihydro-5-oxo-1,3,4-oxadiazol-2-yl) phenyl]amino]-2-chlorophenyl]ethyl]-N-hydroxyacetamide; m.p. 186°–189° C. dec.

The following compounds are prepared according to a procedure analogous to that of Example 13 using appropriate corresponding starting materials.

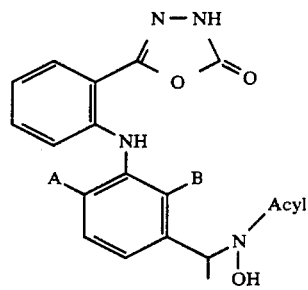

| Prepared from Compound of Example | Example | A | B | Acyl | % Yield | M.P. °C. |
|---|---|---|---|---|---|---|
| 2 | 14 | H | H | Ac | 43 | 185–187 dec. |
| 3 | 15 | H | Cl | CO$_2$Et | 21 | 95–100 |
| 4 | 16 | H | Cl | CONHMe | 13 | 200–203 dec. |

EXAMPLE 17

N-[1-[3-[[2-(5-Amino-1,3,4-oxadiazol-2-yl) phenyl]amino]-2-chlorophenyl]ethyl]-N-hydroxyacetamide To a solution of 2-[[3-[1-(acetylhydroxyamino)ethyl]-2-chlorophenyl]amino]benzoic acid hydrazide (0.35 g, 0.9 mmoles) in 20 mL of dioxane is added a solution of sodium bicarbonate (0.08 g, 0.9 mmoles) in 5 mL of water. Cyanogen bromide (0.1 g, 1.0 mmoles) is added to the reaction mixture, which is then stirred at room temperature overnight. The solution is diluted with 200 mL of water and cooled in an ice water bath for 10 minutes. The precipitate is collected and purified by flash chromatography (10% MeOH/CHCl$_3$ over silica gel). Yield=0.13 g (37%) of N-[1-[3-[[2-(5-Amino 1,3,4-oxadiazol-2-yl) phenyl]amino]-2-chlorophenyl]ethyl]-N-hydroxyacetamide, m.p. 142°–146° C.

We claim:

1. A compound of the Formula (I)

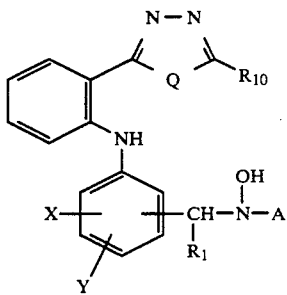

I or a pharmaceutically acceptable salt thereof; wherein
Q is S or O;
R$_{10}$ is —OH, —SH, or —NH$_2$;
R$_1$ is H or lower alkyl;
X is H, halogen, lower alkyl, lower alkoxy, CF$_3$, or OH;
Y is H, halogen, lower alkyl, lower alkoxy, CF$_3$, or OH;

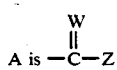

wherein
W is S or O,
Z is lower alkyl, lower alkoxy, NR$_2$R$_3$
wherein R$_2$ and R$_3$ are independently H or lower alkyl.

2. A compound of claim 1 wherein Q is S.
3. A compound of claim 1 wherein Q is O.
4. A compound of claim 1 wherein W is O.
5. A compound of claim 1 wherein W is S.
6. A compound of claim 1 wherein R$_{10}$ is OH.
7. A compound of claim 1 wherein R$_{10}$ is SH.
8. A compound of claim 1 wherein R$_{10}$ is NH$_2$.
9. A compound of claim 3 which is N-[1-[2-chloro-3-[[2-(4,5-dihydro-5-thioxo-1,3,4-oxadiazol-2yl) phenyl]amino]phenyl]ethyl]-N-hydroxyacetamide.
10. A compound which is the monosodium salt of the compound of claim 9.
11. A compound of claim 3 which is N-[1-[3-[[2-(4,5-dihydro-5-thioxo-1,3,4-oxadiazol-2-yl) phenyl]amino]-2-methylphenyl]ethyl]-N-hydroxyacetamide.
12. A compound of claim 3 which is N-[1-[3-[[2-(4,5-dihydro-5-thioxo-1,3,4-oxadiazol-2-yl) phenyl]amino]-2,6-dimethylphenyl]ethyl]-N-hydroxyacetamide.
13. A compound of claim 3 which is N-[1-[3-[[2-(4,5-dihydro-5-thioxo-1,3,4-oxadiazol-2-yl) phenyl]amino]-phenyl]ethyl]-N-hydroxyacetamide.
14. A compound of claim 3 which is the ethyl ester of [1-[2-chloro-3-[[2-(4,5-dihydro-5-thioxo-1,3,4-oxadiazol-2-yl) phenyl]amino]phenyl]ethyl]hydroxycarbamic acid.
15. A compound of claim 3 which is N-[1-[2-chloro-3-[[(4,5-dihydro-5-thioxo-1,3,4-oxadiazol-2-yl) phenyl]amino]phenyl]ethyl]-N-hydroxy-N'-methylurea.
16. A compound of claim 3 which is N-[1[2-chloro-3-[[2-(4,5-dihydro-5-oxo-1,3,4-oxadiazol-2-yl) phenyl]amino]phenyl]ethyl]-N-hydroxyacetamide.
17. A compound of claim 3 which is N-[1-[3-[[2-(4,5-dihydro-5-oxo-1,3,4-oxadiazol-2-yl) phenyl]amino]-phenyl]ethyl]-N-hydroxyacetamide.
18. A compound of claim 3 which is the ethyl ester of [1-[2-chloro 3-[[2-(4,5-dihydro-5-oxo-1,3,4-voxadiazol-2-yl) phenyl]amino]phenyl]ethyl]hydroxycarbamic acid.
19. A compound which is the sodium salt of the compound of claim 18.
20. A compound of claim 3 which is N-[1-[2-chloro-3-[[2-(4,5-dihydro-5-oxo-1,3,4-oxadiazol-2-yl) phenyl]amino]phenyl]ethyl]-N-hydroxy-N'-methylurea.
21. A compound of claim 3 which is N-[1-[2-chloro-3-[[2-(5-amino-1,3,4-oxadiazol-2-yl) phenyl]amino]-phenyl]ethyl]-N-hydroxyacetamide.
22. A pharmaceutical composition for the treatment of conditions advantageously affected by the inhibition of one or both of 5-lipoxygenase and cyclooxygenase which comprises an amount effective for the treatment of the condition of the compound of claim 1 together with a pharmaceutically acceptable carrier.
23. A method for the treatment of the condition in a human which condition is advantageously affected by the inhibition of one or both of 5-lipoxygenase and cyclooxygenase comprising administering the compound of claim 1 in unit dosage form.

* * * * *